United States Patent [19]

LeBlanc

[11] Patent Number: 4,921,853

[45] Date of Patent: May 1, 1990

[54] METHOD FOR PRODUCING ANALGESIA IN MAMMALS

[75] Inventor: Patrick H. LeBlanc, Okemos, Mich.

[73] Assignee: Michigan State University, East Lansing, Mich.

[21] Appl. No.: 271,128

[22] Filed: Nov. 14, 1988

[51] Int. Cl.$^6$ ............................................. A61K 31/54
[52] U.S. Cl. .................................................. 514/227.2
[58] Field of Search ........................................ 514/222

[56] References Cited

PUBLICATIONS

W. V. Lumb and E. W. Jones, "Spinal Anesthesia" in Veterinary Anesthesia, 1984, pp. 400–402.

T. L. Yaksh, "Pharmacology of Spinal Adrenergic Systems which Modulate Spinal Nociceptive Processing", Pharmacology Biochemistry & Behavior, vol. 22, pp. 845–858, 1985.

Fleetwood-Walker et al., "An A$_2$ Receptor Mediates the Selective Inhibition by Noradrenaline . . . ", Brain Research, vol. 334, pp. 243–254, 1985.

D. W. Coombs, et al., "Intrathecal Morphine Tolerance: Use of Intrathecal Clonidine . . . ", Anesthesiology, vol. 62, pp. 358–363, 1985.

D. B. Brunson et al., "Comparative Analgesia of Xylazine, Xylazine/Morphine, Xylazine/Butorphanol . . . ", Am. Journ. Vet. Res., vol. 48, pp. 1087–1091, 1987.

W. W. Muir, et al., "Effect of Xylazine on Indices of Myocardial Contractility in the Dog", Am. Journ. Vet. Res., vol. 38, pp. 931–934, 1977.

F. B. McCashin, et al., "Evaluation of Xylazine as a Sedative and Preanesthetic Agent in Horses", Am. Journ. Vet. Res., vol. 36, pp. 1421–1429, 1975.

*Primary Examiner*—Stanley J. Friedman
*Attorney, Agent, or Firm*—Joseph C. Gil; Lyndanne M. Whalen

[57] ABSTRACT

A method for administering xylazine to a mammal in which xylazine is injected in the subarachnoid space or in the caudal epidural space of the mammal. This method produces analgesia and less extraspinal side effects such as sedation, ataxia and cardiovascular depression.

12 Claims, 2 Drawing Sheets

METHOD FOR PRODUCING ANALGESIA IN MAMMALS

BACKGROUND OF THE INVENTION

The present invention relates to a method for producing analgesia in mammals, particularly larger mammals such as horses and cattle.

Local anesthetic drugs are used to produce spinal (I.E. subarachnoid) or epidural caudal analgesia for a number of diagnostic and surgical procedures performed on horses, cattle, sheep, etc. These drugs depress axonal conduction. Sympathetic, sensory and motor fibers are affected in order of decreasing sensitivity. Such non-specific action may result in limb weakness when motor fibers are affected. Spinal or epidural caudal analgesia using local anesthetics in horses or cattle may produce marked ataxia or even recumbency (See, e.g., Lumb W. V. and Jones E. W. "Spinal Anesthesia" in *Veterinary Anesthesia*, 1984, pages 400–402). It would be advantageous to have a drug effective for spinal or caudal epidural analgesia which produces blockade of sensory fibers without affecting sympathetic or lower motor innervation.

The experimental administration of adrenergic agents such as norepineephrine in the epidural space results in significant analgesia in various animals (See, e.g, Yaksh, T. L., "Pharmacology of Spinal Adrenergic Systems Which Modulate Spinal Nociceptive Processing", *Pharmacol. Biochem. Behav.* Vol. 22, pages 845–858 (1985)). This effect is mediated by spinal alpha 2 adrenergic receptors because analgesia is blocked by alpha 2 (but not alpha 1) antagonists. (See, e.g., Fleetwood-Walker, S. M. et al, "An Alpha 2 Receptor Mediates the Selective Inhibition by Noradrenaline of Nociceptive Responses of Identified Dorsal Horn Neurones" *Brain Res.,* Vol. 334, pages 243–254 (1985)). Alpha 2 receptors inhibit the release of a spinal neurotransmitter which is believed to be important in pain perception (See, e.g, Pernow, B. "Substance P", *Pharmacol. Rev.* Volume 35 pages 85–141 (1983)).

There is clinical significance to the inhibition of spinal transmission of painful stimuli by using spinal or epidural alpha 2 adrenergic agonists. These clinical advantages of spinal or epidural alpha 2-induced analgesia include: (1) attenuation of the extraspinal side effects associated with the systemic administration of alpha 2 agents (respiratory and cardiovascular depression), (2) prolonged duration of action and (3) absence of diminished hind limb strength. Spinal alpha 2-induced analgesia has been achieved with clonidine, an alpha agonist used clinically to control hypertension. (See, e.g., Coombs, D. W. et al, "Intrathecal Morphine Tolerance; Use of Intrathecal Clonidine, DADLE, and Intraventricular Morphine", *Anesthesiology*, Volume 62, pages 358–363 (1985)).

Xylazine is an alpha 2 adrenergic agonist which is commonly used parenterally for sedation and analgesia in horses and other mammals. Xylazine produces analgesia comparable to morphine (See, e.g, Brunson, D. B., et al, "Comparative Analgesia of Xylazines, Xylazine/Morphine, Xylazine/Butorphanol, and Xylazine/Nalbulphine in the Horse, Using Dental Dolorimetry", *AJVR*, Volume 48, pages 1087–1091 (1987)), dose dependent cardiovascular depression (See, e.g., Muir et al, "Effect of Xylazine on Indices of Myocardial Contractility in the Dog", *AJVR*, Volume 38, pages 931–934 (1977)) and profound sedation (See, e.g., McCashin, F. B. et al, "Evaluation of Xylazine as a Sedative and Preanesthetic Agent in Horses", *AJVR*, Volume 36, pages 1421–1429 (1975)). Until now, however, no one has determined whether xylazine administered spinally or epidurally could result in spinal or epidural caudal analgesia without extraspinal side effects such as sedation, ataxia and cardiovascular depression.

SUMMARY OF THE INVENTION

It is an object of the present invention to provide a method for spinally (i.e. directly into the fluid around the spinal cord) or epidurally administering an analgesic to a mammal which results in caudal analgesia and less extraspinal side effects such as sedation, ataxia and cardiovascular depression.

It is also an object of the present invention to provide a spinal or an epidural analgesic which causes less extraspinal side effects such as sedation, ataxia and cardiovascular depression.

These and other objects which will be apparent to those skilled in the art are accomplished by injecting xylazine in the subarachnoid or epidural caudal space of a mammal in an effective dose.

DETAILED DESCRIPTION OF THE INVENTION

Figure 1:
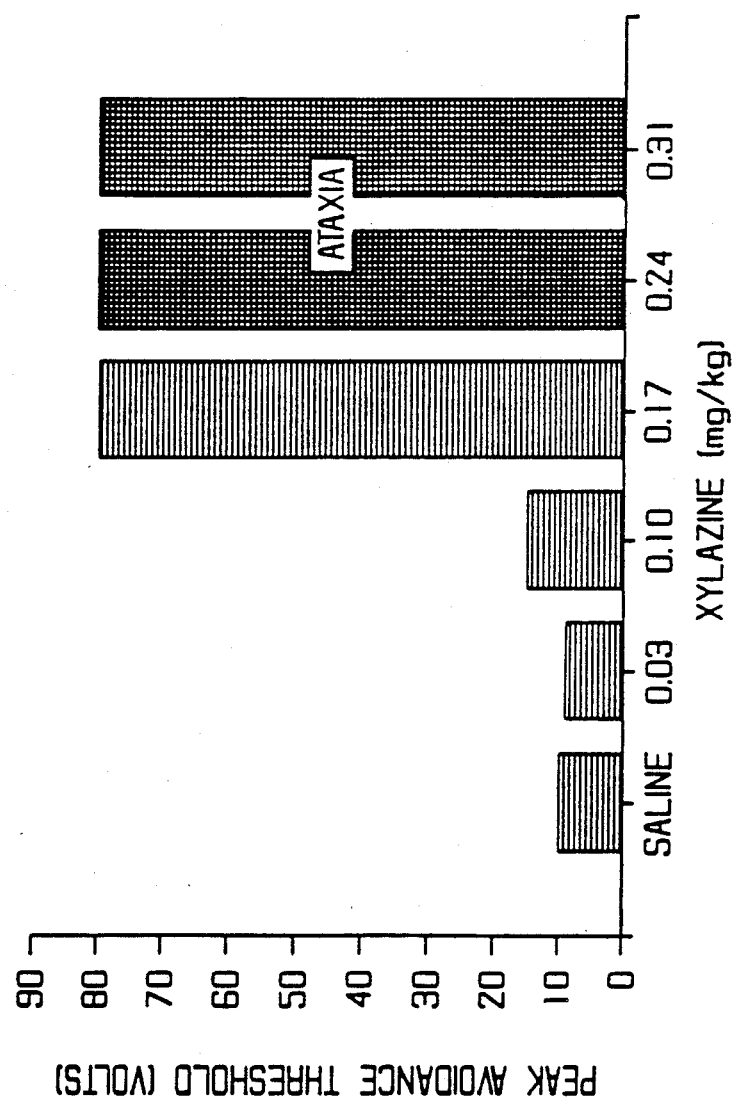
FIG. 1 is a graph illustrating the average peak avoidance threshold of horses for saline and five different concentrations of xylazine administered in the caudal epidural space.

The present invention is directed to a method for achieving spinal or epidural caudal analgesia in mammals. This method is particularly useful for achieving spinal or caudal epidural analgesia in large mammals such as horses and cattle but may also be used on smaller mammals. More specifically, it has been found that epidural administration of xylazine in an appropriate amount results in caudal analgesia without the behavioral effects commonly associated with systemically administered xylazine. It has also been found that administration of xylazine in the subarachnoid space in an appropriate amount results in analgesia without sedation or ataxia.

The method of the present invention is suitable for use in all mammals particularly animals such as swine, goats, horses, cattle, deer, elk, dogs, cats and sheep. The fact that this invention is discussed in great detail with specific examples to horses and cattle should not therefore be construed as a limitation for the process of the present invention to only those specific animals.

Xylazine which is also known as N-(2,6-dimethylphenyl)-5,6-dihydro-4H-1,3-thiazin-2-amine is represented by the formula

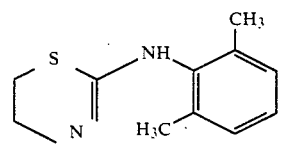

and is commercially available under the name Rompun from Mobay Corporation.

The appropriate dose of xylazine to be administered in accordance with the present invention for a particular animal will depend upon the particular type of animal, its size and the type of injection (i.e. whether epidural or subarachnoid space) but may be readily determined by one of ordinary skill in the art.

For example, it has been found that xylazine administered in the caudal epidural space of horses in a dose of 0.10 mg/kg xylazine or less failed to produce any significant analgesic effect. Doses in excess of 0.24 mg/kg xylazine commonly cause moderate hind limb ataxia and may not therefore be desirable in all cases. A dose of 0.4 mg/kg xylazine produced severe ataxia but not recumbency. Doses of from about 0.11 to about 0.24 mg/kg xylazine resulted in good analgesic effect with infrequent mild ataxia and no sedation in all horses and are therefore generally preferred. Doses of from about 0.15 to about 0.20 are particularly preferred for horses.

It has also been found that xylazine administered in the caudal epidural space of cattle in a dose of less than 0.05 mg/kg produced analgesia inconsistently. Doses of 0.12 mg/kg xylazine produced noticeable ataxia but not recumbency. Doses above 0.05 and below 0.12 mg/kg xylazine produce consistent epidural analgesia with minimal side effects such as sedation and ataxia. Therefore, in cattle, the preferred dose of xylazine is generally from about 0.05 mg/kg to 0.12 mg/kg.

It has further been found that substantially smaller doses are required where xylazine is administered in the subarachnoid space. For example, in cattle, a dose as low as about 0.004–0.006 mg/kg xylazine in 5 ml of isotonic saline injected in the spine will result in analgesia without sedation or ataxia. The appropriate dose for a specific animal may be readily determined by one skilled in the art.

In addition to xylazine, known carriers and nonactive materials which are commonly used by those skilled in the art such as isotonic saline solution may also be included in the preparation which is administered in accordance with the present invention.

Techniques for administering subarachnoid and epidural analgesics such as axylazine are known to those skilled in the art. Such techniques are disclosed, for example, in Lumb, W. V. et al, "Spinal Anesthesia" in *Veterinary Anesthesia*, 2nd Ed. pages 393–411 (1984).

Having thus described the invention, the following Examples are given as being illustrative thereof.

EXAMPLES

Example A

Determination of the Effective Dose of Xylazine to be Administered In The Caudal Epidural Space of Horses Thirty adult horses were randomly assigned one of six treatments. The blinded treatments were given in the epidural space between the 1st and 2nd coccygeal vertebrae with a 20 gauge 3.7 cm hypodermic needle. Confirmation of proper needle placement was based on evidence of negative pressure (hanging drop technique) and negligible resistance to injection. The treatments given in equal volumes (10 ml) were: (1) Saline, (2) 0.03 mg/kg xylazine (Rompun from Mobay Corporation, Shawnee, KS (xyl)), (3) 0.10 mg/kg xyl, (4) 0.17 mg/kg xyl, (5) 0.24 mg/kg xyl and (6) 0.31 mg/kg xyl.

An electrical stimulus was applied to the unsedated horse using a square wave direct current nerve stimulator (Grass SD9 Stimulator, Grass Instruments, Quincy, MA 02169) attached to the horse with two alligator clip electrodes. The electrodes were placed 10 cm apart on either side of and approximately 3 cm below the anus. During testing, voltage (0.5 ms duration) was increased until a clear avoidance response (avoidance threshold) was apparent to two blinded observers. The avoidance threshold (AT) was recorded immediately prior to treatment (baseline) and at 15 minute intervals for at least 120 minutes or until the avoidance threshold returned to baseline. The maximum stimulus applied was 80 volts (V) to avoid tissue damage. The treatment that produced the highest avoidance threshold in the absence of other side effects was chosen as EDxyl. Based on pilot studies, it was determined that an avoidance threshold of 40 V or greater corresponded to analgesia sufficient for skin incision, so a minimum avoidance threshold of 40 V was considered necessary for the does to be relevant. This electrical stimulation method of testing fulfilled the general criteria of an effective pain model in horses and has been used in sheep.

The average peak avoidance threshold for saline and five concentrations of xylazine is illustrated in FIG. 1. Each bar represents the mean for five horses. Treatments 1, 2 and 3 (saline, and 0.03 and 0.10 mg/kg xylazine) failed to produce an avoidance threshold of 40 V and received no further study. Treatments 5 and 6 (0.24 and 0.31 mg/kg xylazine) commonly caused moderate hind limb ataxia. Epidural xylazine at 0.17 mg/kg (treatment 4) resulted in a peak avoidance threshold of at least 80 V and infrequently produced ataxia, therefore this treatment was selected as the effective dose of epidural xylazine (EDxyl). Sedation was not observed in any of the horses and the ataxia observed using EDxyl (0.17 mg/kg) was inconsistent and mild. Epidural xylazine at 0.4 mg/kg was injected in pilot studies. This dose produced severe ataxia but not recumbency.

Epidural xylazine caused a dose-related area of perineal sweating. The sweating corresponded both temporally and topographically with the region of analgesia.

EXAMPLE B

Onset, Duration and Intensity of Analgesia of EDxyl vs Epidural Lidocaine

Each of 22 horses received one of three treatments. The treatments and electrical stimuli were administered as previously described. The three treatments were: I-(control) Saline, II-0.45 mg/kg lidocaine (Lidocaine Injectable, Vet Labs Ltd., Inc., Lenexa, KS 66215), III-EDxyl (determined in Example A). All treatments were administered as 10 ml of volume and were blinded to the two observers. The avoidance threshold was recorded before and at 15 minute intervals following the injections for at least 120 minutes or until the avoidance threshold returned to baseline. The mean duration of AV>40 V for EDxyl and lidocaine was compared with a Students T test, and the magnitude of the avoidance thresholds compared at 15 minute intervals with a Kruskal-Wallis H test for nonparametric data.

The margins of the desensitized area were determined by response to skin prick using a 20 gauge hypodermic needle. Observations of the systemic and local effects to the drugs were also recorded. At 30 minute intervals after the epidural injection, the horses were walked in tight circles and a subjective assessment of ataxia (absent, mild or severe) was made.

All 9 horses treated with epidural lidocaine were severely ataxic in the hind limbs and two became recumbent. Mild hind limb ataxia were observed in 3 of 8 horses treated with EDxyl.

Figure 2:
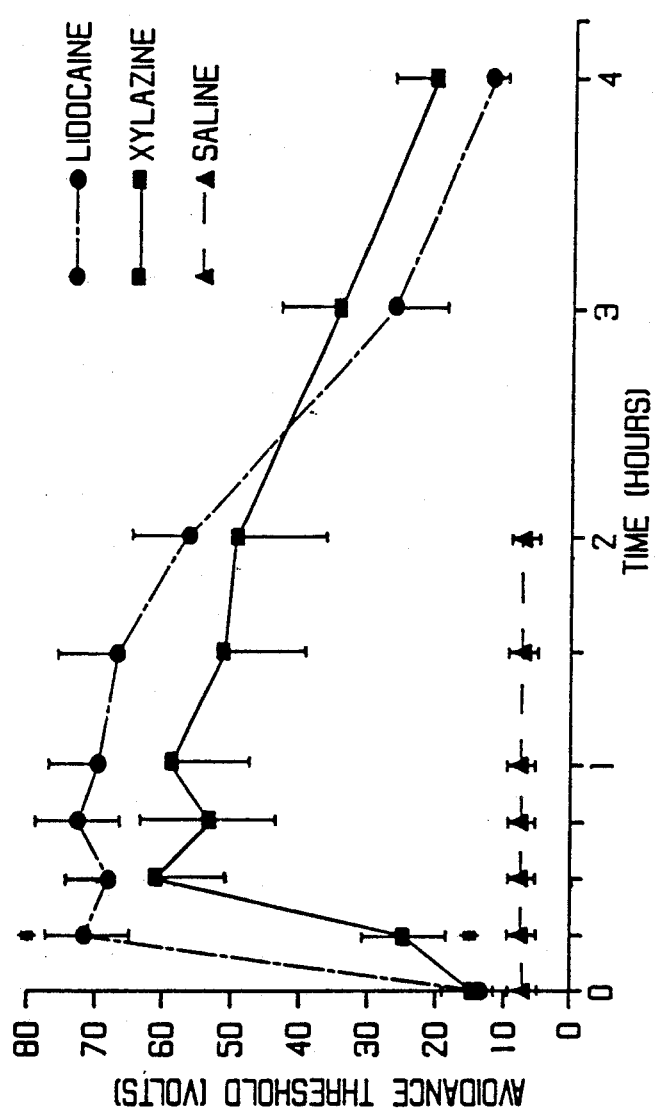
FIG. 2 is a graph on which the average avoidance thresholds of horses for epidural lidocaine and epidural xylazine have been plotted.

The average avoidance thresholds for epidural lidocaine and EDxyl was plotted (FIG. 2). Lidocaine resulted in a significant elevation of the avoidance threshold at 15 minutes (71.6 vs. 25.0 V for xylazine). Analgesia persisted for 2.5±0.7 and 2.6±1.2 hrs ($\bar{X}$±SD) for lidocaine and xylazine, respectively. The duration of each drug's analgesic effect was not therefore significantly different. The area of desensitization to skin prick from EDxyl treatment compared to epidural lidocaine extended approximately 10 cm more cranial on both sides. All horses exhibited a typical avoidance response to skin prick in areas not desensitized.

These results clearly demonstrate that the epidural administration of xylazine results in caudal analgesia in the horse. Analgesia occurred in the absence of behavioral effects commonly associated with systemically administered xylazine.

The observed dermatome of sweat in epidural xylazine-treated horses is unexplained. Systemic xylazine may cause generalized sweating in horses. Xylazine-induced sweating may be the result of an autonomic imbalance favoring alpha adrenergic stimulation. An advantage of this sweat pattern is an indicator of proper epidural injection. Perineal sweating does not occur if the injection is made outside the epidural space. There was a direct correlation between the presence of perineal sweat and caudal analgesia.

0.17 mg/kg of xylazine, approximately 75 mg in a 10 ml volume of diluent for an average-sized adult light breed horse, produced approximately 2.5 hours of AT>40 V. Slight variations in the treatment doses may have occurred since equal volumes of the treatments were administered regardless of the horses size. This variable was minimized by selecting horses of similar size and randomized treatments. The magnitude of the avoidance threshold increase was similar to that produced by epidural lidocaine. Clinically, the 0.17 mg/kg dose of xylazine seems to provide analgesia for substantially longer than lidocaine. Epidural xylazine (0.17 mg/kg in 0.75% solution) was used clinically in 5 mares requiring caudal analgesia for urogenital procedures. These procedures required up to 3.5 hours of analgesia. A single injection of epidural xylazine resulted in appropriate caudal analgesia for all cases. Past clinical experience with a single injection of epidural lidocaine suggests its duration of analgesia would be insufficient for procedures lasting longer than 2 hours. Therefore, epidural xylazine has a much longer duration of analgesia than epidural lidocaine in a clinical situation. The discrepancy between the experimental results and our clinical observations may be related to the testing methods.

It is believed that the site of action for alpha 2-mediated analgesia achieved with xylazine in a mammal such as a horse is intraspinal. The perineal area stimulated in horses is predominantly innervated by the following lumbar spinal nerves: ilohypogastric, ilioinguinal, genitofemoral and caudal cutaneous femoral nerve. The origin of these nerves are lumbar segments L1–L4. Motor innervation to the equine hind limbs is predominantly from the femoral and sciatic nerves. These nerves originate from spinal segments L4 to S1. Analgesia of the area stimulated required xylazine extended cranially enough in the spinal cord to block hind limb motor innervation of it had the capacity to do so. Spinal cord-mediated analgesia by xylazine and spinal nerve-mediated analgesia by lidocaine could result in the differences in analgesic onset and patterns observed in this study. Hind limb ataxia without sedation was observed with high doses of epidural xylazine. This motor involvement may be related to a local anesthetic property of xylazine. Therefore an alternative proposal for the mechanism or epidurally administered xylazine-induced analgesia could be a local anesthetic phenomenon.

Epidural xylazine appears to have a wide margin of safety. In a pilot study, horses receiving greater than twice the EDxyl were no more ataxic than horses receiving epidural lidocaine (0.45 mg/kg). Fortunately, EDxyl produced satisfactory analgesia with a limited incidence of mild ataxia compared to that produced by lidocaine. The lidocaine dose selected represents a commonly used dose.

EXAMPLE C

Effects of Caudal Epidural Administration of Xylazine on the Spinal Cord of Horses It is known that high concentrations of an alpha 2 agonist did not decrease the lumbar spinal cord blood flow in awake sheep. This suggests that alpha 2 agonists would not produce adverse effects to the spinal cord of horses. However, unlike previous studies, a preservative-free alpha 2 solution was not used in the Examples given above and is not required in the present invention. A commercial preparation of xylazine (sold under the trademark Rompun by Mobay Corporation) was used. In a study conducted with three horses, xylazine administered in the caudal epidural space did not alter gross or histologic appearance of the spinal cord or nerve roots.

EXAMPLE D

Effect of Caudal Epidural Administration of Xylazine on the Cardiopulmonary Parameters of Horses Cardiopulmonary parameters (i.e., systemic arterial pressures, arterial gas tensions, heart and respiratory rates) were measured in 6 horses which had received an intravenous bolus injection of 0.17 mg/kg xylazine. A transient second degree heart block was produced.

Horses injected with the same dosage of xylazine in the caudal epidural space showed no significant electrocardiographic changes. No changes in systemic arterial pressures, arterial gas tensions, heart and respiratory rates were observed in the horses which had been injected with 0.17 mg/kg xylazine in accordance with the present invention.

It may therefore be concluded that at this dose, xylazine given in the caudal epidural space of horses does not cause any cardiovascular or respiratory depression.

In summary, the epidural administration of xylazine (0.17 mg/kg in 0.75% solution) produces caudal analgesia in the horse. The analgesia is produced with mild and infrequent ataxia, no sedation and no cardiovascular or respiratory depression. The effect is similar in duration to epidural lidocaine. Mild side effects were apparent with epidural xylazine (mild ataxia in 3 of 8 horses) compared with a 100% incidence of severe ataxia resulting from epidural lidocaine. Xylazine appears to be superior to lidocaine as an epidural analgesic in the horse.

EXAMPLE E

Determination of Effective Dose of Xylazine for Caudal Epidural Administration in Cattle Each of 25 mature Holstein cows (475–550 kg) was given a single epidural injection of one of four different concentrations of xylazine or a control saline solution. The injections were given in the first coccygeal interspace. Xylazine solutions at concentrations of 1 mg/ml, 3 mg/ml, 5 mg/ml and 7 mg/ml were each diluted with sterile isotonic saline solution to a final volume of 5.0 ml and administered to the cows as described above. All of the treatments were blinded.

The onset, magnitude and duration of analgesia were quantitatively determined by means of a low voltage DC current applied to the perineal area of each cow. The electrodes were placed approximately 5 cm on either side of the vulva. The lowest voltage that produced a clear avoidance response (avoidance threshold) was recorded by two observers. A maximum stimulus of 80 volts was used and clinical analgesia was determined to correspond to approximately 40 volts. The cows were tested immediately prior to the epidural injection (baseline) and at 15 minute intervals thereafter for a minimum of 1.5 hours or until the avoidance threshold returned to baseline. The dose that produced the longest duration of analgesia and produced the least ataxia or sedation was compared to epidural lidocaine.

Seven randomly selected Holstein cows, of similar weights, were given as epidural injection of 100 mg of lidocaine hydrochloride (5.0 ml of a 2% solution). The analgesia produced by epidural lidocaine was compared to 7 cows receiving 25 mg of epidural xylazine (approx. 0.05 mg/kg). Avoidance thresholds were determined in the same manner as previously described.

The mean duration of avoidance threshold elevation (>40 V) was compared using a Student's T test. The magnitude of avoidance threshold was compared with a Kruskal-Wallis H test. Statistical significance was set at the 5% level.

To investigate the possibility that the analgesic properties of epidural xylazine may be the result of systemic absorption, 25 mg of xylazine in 5.0 ml of saline were given intramuscularly to 4 adult cows and 4 cows were given in intramuscular injection of 5.0 ml of saline. Avoidance threshold data was determined. The magnitude of the avoidance thresholds at each interval were statistically compared in the same as described above in Example B.

An epidural dosage of 25 mg of xylazine in 5 ml of diluent (approx. 0.05 mg/kg) provided consistent epidural analgesia (elevation of avoidance threshold) with minimal side effects (sedation/ataxia), however mild sedation was observed in all cows receiving 25 mg of epidural xylazine. Lower doses produced analgesia inconsistently, and a higher dose did not result in an increased duration of analgesia.

Epidural xylazine produced a significantly greater duration of avoidance threshold exceeding 40 V than epidural lidocaine (2.54+/−0.23 hr vs. 0.62+/−0.45 hr). The onset of elevation in the avoidance threshold occurred sooner with lidocaine than xylazine, however this difference was not significant. The avoidance threshold voltage was significantly greater with xylazine than lidocaine from 1.25 hours through 3 hours post-injection. Two of the cows treated with lidocaine were noticeably ataxic and one became recumbent.

Elevation of the avoidance threshold was significantly greater in cattle treated with epidural xylazine compared to those treated intramuscularly. An avoidance threshold exceeding 40 V was recorded only once in a single cow 30 minutes following intramuscular injection. Sedation was more obvious in cattle treated intramuscularly than those treated epidurally.

The mean duration of avoidance threshold elevation produced by xylazine was approximately 4 times that of lidocaine. The relatively high standard error of the means related to marked individual variation within both groups and small sample sizes. The magnitude of elevation of the avoidance threshold was comparable. Avoidance thresholds were usually absent following an electrical stimulus of 80 V DC in both epidural lidocaine and epidural xylazine groups.

An undesirable side effect of epidural xylazine was sedation which may have been due to systemic absorption. Dosages that did not result in sedation inconsistently produced caudal analgesia. Higher doses produced more pronounced sedation, however, recumbency was observed in a single cow, which rose when encouraged. Preliminary studies were conducted using xylazine at higher doses in cattle and injections of 0.12 mg/kg (60 mg xylazine in 5 ml diluent in 500 kg cows) produced noticeable ataxia, but not recumbency. Preferred doses for cattle range from about 0.05 to about 0.15 mg/kg.

The use of xylazine as an epidural analgesic is of considerable clinical utility because of the prolonged duration of analgesia compared to a single epidural dose of lidocaine, and less sedation with greater analgesia compared to the same dose of xylazine administered intramuscular.

EXAMPLE F

Spinal Administration of Xylazine

Xylazine was injected in the spinal canal between the last lumbar and first sacral vertebrae of five cattle. The dose was 0.004–0.006 mg/kg of xylazine in 5 ml of isotonic saline. Analgesia on both sides and underneath the cow without sedation or ataxia occurred at 30 minutes and persisted for at least three hours in each cow.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for achieving analgesia in a mammal comprising injecting an effective dose of xylazine in the caudal epidural space of the mammal or in the subarachnoid space of the mammal.

2. The method of claim 1 in which the xylazine is injected in the caudal epidural space of the mammal.

3. The method of claim 2 in which the mammal is a horse.

4. The method of claim 3 in which the xylazine is administered in a dose of greater than 0.10 mg/kg.

5. The method of claim 3 in which the xylazine is administered in a dose of from about 0.11 to about 0.20 mg/kg.

6. The method of claim 2 in which the mammal is a member of the bovine species.

7. The method of claim 6 in which the xylazine is administered in a dose of at least 0.05 mg/kg.

8. The method of claim 6 in which the xylazine is administered in a dose of from about 0.05 mg/kg to about 0.15 mg/kg.

9. The method of claim 1 in which the xylazine is injected in the subarachnoid space of the mammal in an effective dose.

10. The method of claim 9 in which the mammal is a horse.

11. The method of claim 9 in which the mammal is a member of the bovine species.

12. The method of claim 11 in which the effective dose is from about 0.004 to about 0.006 mg/kg of xylazine.

* * * * *